US007427585B2

(12) United States Patent
Kuroda

(10) Patent No.: US 7,427,585 B2
(45) Date of Patent: Sep. 23, 2008

(54) FRAMED SOAP COMPOSITIONS

(75) Inventor: Shigeru Kuroda, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/768,016

(22) Filed: Feb. 2, 2004

(65) Prior Publication Data

US 2004/0157756 A1 Aug. 12, 2004

(30) Foreign Application Priority Data

Feb. 7, 2003 (JP) ............................ 2003-030768

(51) Int. Cl.
*A61K 7/50* (2006.01)

(52) U.S. Cl. ...................... 510/141; 510/145; 510/146; 510/152

(58) Field of Classification Search ................. 510/141, 510/147, 151, 152, 153, 155
See application file for complete search history.

(56) References Cited

U.S. PATENT DOCUMENTS

| | | | | |
|---|---|---|---|---|
| 4,439,355 | A * | 3/1984 | Kenkare | 510/145 |
| 5,219,487 | A | 6/1993 | Heile, Jr. et al. | |
| 5,703,026 | A * | 12/1997 | Setser et al. | 510/152 |
| 5,952,289 | A * | 9/1999 | Wise et al. | 510/450 |
| 5,972,860 | A | 10/1999 | Eshita et al. | |
| 6,878,319 | B2 * | 4/2005 | Browne et al. | 264/71 |

FOREIGN PATENT DOCUMENTS

| | | |
|---|---|---|
| JP | 10-168494 | 6/1998 |
| JP | 11-172297 | 6/1999 |
| JP | 2000-309795 | 11/2000 |
| JP | 2001-64690 | 3/2001 |
| JP | 2001-64691 | 3/2001 |
| JP | 2002-12898 | 1/2002 |
| JP | 2002-80896 | 3/2002 |
| WO | WO 96/04360 | 2/1996 |
| WO | WO 97/22684 | 6/1997 |

* cited by examiner

*Primary Examiner*—Necholus Ogden
(74) *Attorney, Agent, or Firm*—Oblon, Spivak, McClelland, Maier & Neustadt, P.C.

(57) ABSTRACT

Framed soap compositions contain water and the following ingredients (A) to (D):

(A) from 25 to 60 wt. % of a fatty acid soap containing not greater than 20 wt. % of insolubles;
(B) from 0.1 to 5 wt. % of sodium chloride;
(C) from 0.1 to 5 wt. % of sodium sulfate; and
(D) from 5 to 30 wt. % of a polyol.

These compositions solidify fast upon production, and have a high hardness after production.

13 Claims, No Drawings

FRAMED SOAP COMPOSITIONS

FIELD OF THE INVENTION

This invention relates to framed soap compositions.

BACKGROUND OF THE INVENTION

A bar soap is produced by melting and mixing raw materials such as a fatty acid soap, a polyol and an inorganic salt to give a neat soap and then solidifying the same. As the inorganic salt out of these raw materials, sodium chloride (e.g., JP-A-2002-80896), sodium sulfate (e.g., JP-A-2001-64690), a hydrogencarbonate and/or carbonate (e.g., JP-A-2001-64691) or the like is used to provide the bar soap with improved foamability and transparency.

The solidification behavior and hardness of the resulting bar soap vary depending upon the kind and proportion of such an inorganic salt. When sodium chloride is used as an inorganic salt, for example, a limitation is imposed on its proportion because, if it is added in a large proportion to provide higher hardness, the neat soap undergoes phase separation. The use of sodium sulfate involves drawbacks such as slow solidification and hence, low productivity. Further, the use of sodium carbonate results in a composition having a high melt viscosity, and thus the productivity gets worse.

There have been proposed soap compositions which use a nonionic surfactant in combination with a fatty acid soap and an inorganic salt for accelerating their solidification (JP-A-10-168494, U.S. Pat. No. 5,972,860). These soap compositions are, however, accompanied by the problem that the use of such nonionic surfactants leads to a cost increase since they are generally more expensive than fatty acid soaps.

It has also been proposed to use an insoluble soap as much as 50% or more of a sodium soap in a fatty acid soap with a view to obtaining a cleansing bar excellent in hardness and transparency (WO 96/04360). However, when an insoluble soap is added in a large proportion, sufficient foaming cannot be produced unless one or more other foaming surfactants are used in combination.

SUMMARY OF THE INVENTION

The present invention provides a framed soap composition which contains water and the following ingredients (A) to (D):

(A) from 25 to 60 wt. % of a fatty acid soap containing not greater than 20 wt. % of insolubles;

(B) from 0.1 to 5 wt. % of sodium chloride;

(C) from 0.1 to 5 wt. % of sodium sulfate; and (D) from 5 to 30 wt. % of a polyol.

DETAILED DESCRIPTION OF THE INVENTION

The present invention relates to a framed soap composition which solidifies fast upon production and has a high hardness after production.

The present inventors have found that the combined use of sodium chloride and sodium sulfate as inorganic salts in particular proportions makes it possible to provide, without needing combined use of any nonionic surfactant, a framed soap composition which solidifies fast upon production, has a high hardness after production and foams well upon use.

Examples of the fatty acid soap for use as ingredient (A) in the present invention include alkali metal salts (e.g., sodium salts, potassium salts, and the like), ammonium salts, alkanolamine salts (e.g., monoethanolamine salts, diethanolamine salts, triethanolamine salts, and the like) of saturated or unsaturated fatty acids having 8 to 22 carbon atoms.

The fatty acid soap (A) contains not greater than 20 wt. % based on the total amount of the fatty acid soap (A), preferably 15 wt. % or less, of insolubles. The insolubles having a content greater than 20 wt. % lead to a deterioration in foaming performance, because a limitation is imposed on the proportion of soap in a soap composition which can be produced by a framing process.

The term "insolubles" as used herein means fatty acid soap components each of which has a Kraft point of 60° C. or higher and is insoluble in water under actual use conditions. Specifically, they correspond to salts of saturated fatty acids having 16 or more carbon atoms, such as palmitic acid and stearic acid.

It is preferable that at least 80 wt. % of the fatty acid soap as ingredient (A) consist of alkali metals, more preferably the sodium salts, of saturated fatty acids such as caprylic acid, capric acid, lauric acid and myristic acid because a smaller proportion of a saturated fatty acid soap makes the solidification difficult. Even more preferably, lauric acid soap accounts for at least 25 wt. % of the whole fatty acid soap (A) because more excellent foamability is available.

Illustrative fatty acids, which make up the fatty acid soap (A), include those available from vegetable oils or fats or animal oils or fats (e.g., palm oil, palm kernel oil, coconut oil, castor oil, soybean oil, cotton seed oil, rapeseed oil, sunflower oil, beef tallow, and fat lard) . Among these, fatty acids available from palm kernel oil or coconut oil are preferred.

Incidentally, the fatty acid soap (A) can be produced by direct saponification of the above-described oil or fat or by neutralization of a fatty acid prepared separately.

One or more fatty acid soaps can be used as ingredient (A). The amount of ingredient (A) ranges from 25 to 60 wt. %, preferably from 30 to 50 wt. % based on the total amount of the framed soap composition. A proportion smaller than 25 wt. % may fail to provide sufficient hardness or foaming, while a proportion greater than 60 wt. %, depending upon the composition of the fatty acid, may result in a neat soap having such a high viscosity that the productivity is impaired.

Sodium chloride as ingredient (B) is contained in the composition in a proportion of from 0.1 to 5 wt. %, preferably from 1 to 4 wt. % based on the whole framed soap composition. A proportion smaller than 0.1 wt. % may fail to provide a sufficient hardness, while a proportion greater than 5 wt. % may result in phase separation of the neat soap.

Sodium sulfate as ingredient (C) is contained in the composition in a proportion of from 0.1 to 5 wt. %, preferably from 0.5 to 4 wt. % based on the whole framed soap composition. A proportion smaller than 0.1 wt. % may fail to provide a sufficient hardness, while a proportion greater than 5 wt. % may result in a neat soap having such a high viscosity that the productivity is impaired, or may result in the deposition of crystals on the surface of the soap during long-term storage, which is not preferred from the standpoint of appearance.

Further, the weight ratio of ingredient (B) to ingredient (C) is preferably from 1:50 to 40:1, more preferably from 1:4 to 6:1 as the resulting neat soap has a low viscosity and provides a soap having a high hardness. In addition, the total content of ingredients (B) and (C) is preferably from 1 to 10 wt. %, more preferably from 1.5 to 8 wt. %, even more preferably from 2 to 7 wt. %, still even more preferably from 2.5 to 6 wt. %, because the resulting soap has a high hardness and good foaming property.

Examples of the polyol for use as ingredient (D) in the present invention include glycerin, sorbitol, xylitol, mannitol, glucose, polyethylene glycol, polypropylene glycol, and water-soluble polysaccharides. The molecular weights of polyethylene glycol and polypropylene glycol are preferably 8,000 or lower. Illustrative of the water-soluble polysaccharides are sucrose and trehalose.

These polyols can be used either singly or in combination. The polyol is contained in the composition in a proportion of from 5 to 30 wt. %, preferably from 10 to 25 wt. % based on the whole framed soap composition. A proportion smaller than 5 wt. % fail to provide a sufficient hardness, while a proportion greater than 30 wt. % may result in a neat soap having such a high viscosity that the productivity is impaired.

In the framed soap composition according to the present invention, a free fatty acid may be incorporated further to provide a milder framed soap composition having superior foaming property. As such a free fatty acid, a fatty acid corresponding to ingredient (A) is preferred. Illustrative are palm kernel fatty acid, coconut fatty acid, and hydrogenated coconut fatty acid. These free fatty acids can be used either singly or in combination. The free fatty acid, when added, maybe contained in the composition in a proportion of preferably from 0.2 to 9 wt. %, more preferably from 0.5 to 5 wt. % based on the whole framed soap composition. Such a free fatty acid may be added as one of ingredients, or alternatively, may be produced in the composition by adjusting the degree of neutralization during production of the fatty acid soap.

The weight ratio of the neutralized fatty acid soap to the free fatty acid may be in a range of from 99:1 to 85:15, with a range of from 98:2 to 90:10 being more preferred, because the resulting foamed soap composition provides improved skin feel and is not too soft.

The molten neat soap may be whipped to subject it to aeration treatment. In this case, the resulting whipped composition is poured into suitable molds or frames. The whipped gas bubbles may, however, collapse in the molds or frames resulting in a liquid phase separation. To avoid such phase separation, it is preferable to further add a hydroxy acid ester surfactant, a monoglyceride surfactant, a sucrose ester surfactant or a lactate ester surfactant to the framed soap composition according to the present invention. Among these, the addition of the lactate ester surfactant is preferred. Such an ester surfactant may be contained preferably in a proportion of from 1 to 10 wt. % based on the whole composition, with from 2 to 5 wt. % being more preferred.

To improve foamability at low temperatures and scum dispersibility, it is also preferred to add a non-soap anionic surfactant. Examples of such an anionic surfactant include alkanoyl isethionate salts, polyoxyethylene alkyl ether sulfates, acylmethyltaurine salts, acyl sarcosinates, sulfosuccinates, monoalkyl phosphate salts, and alkanoyl-β-alanine salts. Such a non-soap anionic surfactant, when used, may be contained preferably in a proportion of from 1 to 20 wt. % based on the whole composition, with from 5 to 15 wt. % being more preferred.

For the purpose of improving the foaming power further, an amphoteric surfactant can also be used. Examples of such an amphoteric surfactant include betaine surfactants, amino acid surfactants, imidazoline surfactants, and amine oxide surfactants. Of these, betaine surfactants are preferred, with alkylamidopropylbetaine and sulfobetaine being more preferred. Such an amphoteric surfactant, when added, may preferably be contained in the composition in a proportion of from 0.1 to 10 wt. % based on the whole composition, with from 1 to 5 wt. % being more preferred.

In the framed soap composition according to the present invention, an organic acid other than fatty acids may be additionally incorporated to stabilize its fragrance. Examples of such an organic acid include lactic acid and gluconic acid. Such an organic acid, when incorporated, may be contained in the composition in a proportion of from 0.01 to 3 wt. % based on the whole composition, with from 0.1 to 1 wt. % being more preferred.

For the purpose of improving the foam smoothness, it is also possible to add a high-molecular compound such as high polymerization-degree polyethylene glycol ("ALKOX E-100", trade name; product of MEISEI CHEMICAL WORKS, LTD.; molecular weight: 2,500,000), a cationic polymer, cellulose, hydroxymethylcellulose, hydroxyethylcellulose, hydroxypropylcellulose, carboxymethylcellulose, or methylcellulose. Among these, high polymerization-degree polyethylene glycol is preferred. The high-molecular compound may be contained in the composition preferably in a proportion of from 0.001 to 5 wt. % based on the whole composition, with from 0.01 to 1 wt. % being preferred.

In addition to the above-described ingredients (A) to (D) and, if any, other optional ingredients, it is also necessary to add water to the framed soap composition according to the present invention so that the ingredients so used can be formed into a uniform melt. During the production, from 25 to 50 wt. % of water is usually contained in the composition. This water is contained in substantially the same proportion in the composition shortly after its production. As the drying proceeds, however, the proportion of water may gradually decrease. Such a drying can be prevented by a suitable package or container, e.g. wrapping with plastic or metal films.

In the framed soap composition according to the present invention, additives known to be usable in conventional cleanser compositions, for example, antimicrobial agents, fragrances, pigments, dyes, oil ingredients and other irritation reducing agents can be contained. Examples of the antimicrobial agents include trichlosan and trichlorocarbanilide. An antimicrobial agent may be contained in the composition generally in a proportion of from 0.1 to 2 wt. %. Fragrance, pigment, dye and the like, on the other hand, may each be contained in the composition generally in a proportion of from 0.2 to 5 wt. %. Examples of the oil ingredients include lanolin, paraffin, vaseline, and isopropyl myristate. An oil ingredient may be contained in the composition generally in a proportion of from 0.5 to 5 wt. %.

The framed soap composition according to the present invention can be produced by any suitable conventional procedure. For example, ingredients (A) to (D) and water as well as other ingredients, if necessary, are stirred under heating at from 65 to 90° C. to melt or dissolve them to form a neat soap. The neat soap is poured, as it is, into molds or frames, cooled and solidified, and then dried to produce a framed soap composition.

When whipped gas bubbles are included to provide a lightweight soap (floating soap), the neat soap obtained as described above is subjected to aeration treatment by a domestic or industrial whipping apparatus so that gas bubbles are entrapped. When aeration treatment is applied by conducting whipping as described above, the solidification rate of the neat soap can be increased further. Accordingly, when the neat soap in this whipped form (in other words, a foamed neat) is poured into molds or frames, the neat soap solidifies as it is without undergoing phase separation. Further, owing to the inclusion of whipped gas bubbles, the resultant framed soap composition is prevented from penetration of water by the gas bubbles and thus is resistant to mush or swelling.

The volume fraction of gas bubbles is preferably 10% or greater, with 30% or greater being more preferred, in view of the solidification rate, hardness, ease of dissolution and the like of the framed soap composition. From the viewpoint of the physical strength of the composition to be obtained, the volume fraction of gas bubbles is preferably 80% or less. The volume fraction of gas bubbles can be determined by pouring a foamed neat in a container of 100 mL in volume, measuring the weight W (g) of the composition, and conducting a calculation based on 100−W.

Concerning the size of gas bubbles, the average bubble size is preferably 80 μm or smaller, more preferably 60 μm or smaller to prevent the resulting framed soap composition from becoming excessively soluble and also to make it resistant to swelling. No particular limitation is imposed on the lower limit of the average bubble size. In view of productivity, however, an average gas bubble size of 10 μm or greater is preferred, with 15 μm or greater being more preferred, when a conventional industrial whipping apparatus is used. Incidentally, an average bubble size can be determined by holding a foamed neat between two plates of slide glass (spacing: 150 to 180 μm), quenching and solidifying the foamed neat there, observing the thus-obtained sample with a microscope using a transmitted light from a backlight to obtain image data, performing measurement of bubble diameters on an image processing software "Image-Pro Plus", and then calculating an average value.

As a gas useful upon conducting the aeration treatment, air, nitrogen or the like can be chosen and used as needed.

The inclusion of whipped gas bubbles in the frame soap composition obtained as a bar soap can be confirmed by one or both of the following methods:

(1) Measure the specific gravity of the bar soap. A specific gravity of less than 1 indicates the inclusion of gas bubbles.

(2) Slice the bar soap with a razor blade, and observe the cut surface with an optical microscope. The inclusion of round gas bubbles, if any, can be observed.

The following examples further describe and demonstrate embodiments of the present invention. The examples are given solely for the purpose of illustration and are not to be construed as limitations of the present invention.

EXAMPLES

Examples 1-7 & Comparative Examples 1-10

Framed soap compositions of the formulations shown in Table 1 were produced, and were evaluated with regard to ease of production, hardness and foaming. The results are also shown in Table 1. The fatty acid compositions of the mixed fatty acid soaps used in the examples are shown in Table 2.

(Production Procedure)

In each example, all the ingredients were molten at from 70 to 80° C., and while paying attention to avoid evaporation of water, the resultant melt was whipped by a hand mixer to prepare a gas bubbled neat. The gas bubbled neat was then poured into a mold of 100-mL volume made of plastics, and allowed to cool down and solidify at room temperature to obtain a framed soap composition. The framed soap compositions of Examples 1-7 obtained as described above all contained gas bubbles.

(Evaluation Methods)

(1) Ease of Production

In each example, the neat soap of 400 mL amount was stirred by a stirring blade in a stainless steel beaker kept warm in a warm water bath controlled at from 70 to 80° C. The neat soap was then poured into four 100-mL plastic molds. The ease of work upon pouring the neat soap was evaluated on the basis of the following criteria:

A: A neat has an adequate viscosity, and is easy to work with.

B: A neat has a high viscosity, or its solidification is slow.

C: A neat has a very high viscosity, or its solidification is very slow.

(2) Hardness

In each example, the neat soap poured into the plastic molds was measured for hardness (unit: kgf/10 mm in diameter) by a rheometer (manufactured by Fudo Industries, Ltd.; equipped with an adapter of 10 mm in diameter) after the neat soap had been allowed to cool down and solidify at room temperature. Hereby, the upper limit of measured hardness is 10, while the lower limit is 0. A hardness of 4.5 or higher is preferred.

(3) Foaming Property

Using warm water at 40° C., expert panelists washed their hands with the framed soap composition in each example. The foaming property of the framed soap composition was evaluated on the basis of the following criteria:

A: Foams well.

B: Foams a little.

C: Foams poorly.

TABLE 1

| | | Examples | | | | | | | Comparative Examples | | | | | | | | | |
|---|---|---|---|---|---|---|---|---|---|---|---|---|---|---|---|---|---|---|
| | Ingredients (wt. %) | 1 | 2 | 3 | 4 | 5 | 6 | 7 | 1 | 2 | 3 | 4 | 5 | 6 | 7 | 8 | 9 | 10 |
| A | Na salt of palm kernel fatty acid | 32 | 50 | 50 | 39 | 32 | 32 | 40 | 50 | 35 | 35 | 35 | 35 | 35 | 35 | 15 | 65 | 30 |
| | Na salt of palm stearic fatty acid | | | | 4 | | | | | | | | | | | | | 20 |
| B | Sodium chloride | 1.2 | 3 | 3 | 1.5 | 0.25 | 5 | 2 | 3 | 5 | | | | | | 3 | 3 | 3 |
| C | Sodium sulfate | 3.6 | 1 | 1.5 | 3 | 0.75 | 5 | 3 | | | 5 | | | | | 1 | 1 | 1 |
| D | Glycerin | 30 | 10 | 10 | 25 | 30 | 30 | | 10 | 10 | 30 | | | | 25 | 25 | 10 | 10 |
| | Sorbitol | | | | | | | 20 | | | | 30 | 30 | 30 | | | | |
| | Sodium carbonate | | | | | | | | | | | 4 | | | | | | |
| | Calcium chloride | | | | | | | | | | | | 4 | | | | | |
| | Magnesium sulfate | | | | | | | | | | | | | 4 | | | | |
| | Water | 33.2 | 36 | 35.5 | 27.5 | 37 | 28 | 35 | 37 | 50 | 30 | 31 | 31 | 31 | 40 | 56 | 21 | 36 |
| Insolubles in whole fatty acid soap (wt. %) | | 13 | 13 | 13 | 17 | 13 | 13 | 13 | 13 | 13 | 13 | 13 | 13 | 13 | 13 | 13 | 13 | 31 |
| Free fatty acid (wt. %)[1)] | | 3 | 1 | 1 | 1 | 3 | 3 | 2.5 | 3 | 3 | 3 | 3 | 3 | 3 | 3 | 1 | 1 | 3 |

TABLE 1-continued

| | Examples | | | | | | | Comparative Examples | | | | | | | | | |
|---|---|---|---|---|---|---|---|---|---|---|---|---|---|---|---|---|---|
| Ingredients (wt. %) | 1 | 2 | 3 | 4 | 5 | 6 | 7 | 1 | 2 | 3 | 4 | 5 | 6 | 7 | 8 | 9 | 10 |
| Foaming property | A | A | A | A | A | A-B | A | A | C | A | C | C | B | A | C | A | B |
| Hardness | 8 | 6.1 | 5 | 7 | 4.5 | 10 | 10 | 4 | 8 | 10 | 9.2 | 0.6 | 0.2 | —[2)] | 3 | —[3)] | 5.1 |
| Ease of production | A | A | A | A | A | A | A | A | C | B | B | C | C | C | A | C | A |

[1)]Total proportion of the free fatty acids contained in the fatty acid soap(s) as ingredient (A), said total proportion being based on the whole composition.
[2)]Too soft to perform the measurement.
[3)]The viscosity of the neat soap was too high to pour it into the frames, and no sample was prepared for the measurement.

TABLE 2

| Contents(wt. %) | | Palm kernel oil fatty acid | Coconut oil fatty acid | Palm stearic fatty acid | Hydrogenated coconut oil fatty acid |
|---|---|---|---|---|---|
| C8 | Caprylic acid | 3-5 | 6-10 | 0-1 | 6-10 |
| C10 | Capric acid | 3-7 | 4-12 | 0-1 | 4-12 |
| C12 | Lauric acid | 44-55 | 45-52 | 0-2 | 45-52 |
| C14 | Myristic acid | 10-17 | 15-22 | 1-2 | 15-22 |
| C16 | Palmitic acid | 6-10 | 4-10 | 50-70 | 4-10 |
| C18 | Stearic acid | 1-7 | 1-5 | 4-6 | 4-18 |
| C18:1 | Oleic acid | 1-17 | 2-10 | 20-35 | 0-1 |
| C18:2 | Linoleic acid | 0-2 | 1-3 | 3-7 | 0-1 |

Example 8

In a similar manner as in Examples 1-7, a framed soap composition of the below-described formulation was produced.

The thus-obtained framed soap composition solidified fast upon production, had a high hardness after the production, and foamed well upon use.

| (Ingredients) | |
|---|---|
| Sodium salt of palm kernel fatty acid | 40.12 (wt. %) |
| Sodium myristate | 3.13 |
| Sodium chloride | 1.97 |
| Sodium sulfate | 2.96 |
| Sorbitol | 20.31 |
| Amidopropylbetaine ("AMPHITOL 20AB", trade name; product of Kao Corporation) | 1.61 |
| Sulfobetaine ("AMPHITOL 20HD", trade name; product of Kao Corporation) | 1.61 |
| High polymerization-degree polyethylene glycol ("ALKOX E-100", product of MEISEI CHEMICAL WORKS, LTD.) | 0.02 |
| BHT | 0.08 |
| Hydroxyethanediphosphonic acid ("DEQUEST 2010CS", trade name; product of Solutia Japan Limited) | 0.24 |
| Fragrance | 1.20 |
| Water | 26.75 |
| (Insolubles in the whole fatty acid soap: | 12 wt. % |
| Free fatty acids in the whole fatty acid soap: | 2.5 wt. %) |

INDUSTRIAL APPLICABILITY

Framed soap compositions according to the present invention solidify fast upon production, have a high hardness after production, and foam well upon use.

What is claimed is:

1. A framed soap composition comprising water and the following ingredients (A) to (D):

(A) from 25 to 60 wt. % of a fatty acid soap containing not greater than 20 wt. % of insolubles;

(B) from 0.1 to 5 wt. % of sodium chloride;

(C) from 0.1 to 5 wt. % of sodium sulfate;

(D) from 5 to 30 wt. % of a polyol selected from the group consisting of glycerin and sorbitol and (E) from 25 to 50 wt. % of water, wherein the total content of ingredients (B) and (C) is from 1 to 10 wt. %, and wherein the weight ratio of ingredient (B) to ingredient (C) is from 1:4 to 6:1; and the composition further comprising from 10 to 80% of a volume fraction of gas bubbles obtained by aeration treatment.

2. The framed soap composition according to claim 1, wherein the fatty acid soap (A) comprises at least 80 wt. % of an alkali metal salt of a saturated fatty acid.

3. The framed soap composition according to claim 1, wherein the fatty acid soap (A) comprises at least 25 wt. % of lauric acid soap.

4. The framed soap composition according to claim 1, wherein a fatty acid of the fatty acid soap (A) is one derived from palm kernel oil or coconut oil.

5. The framed soap composition according to claim 1, further comprising from 0.2 to 9 wt. % of a free fatty acid.

6. The framed soap composition according to any one of claims 1-4, or 5, which does not contain a nonionic surfactant.

7. The framed soap composition according to claim 1, wherein the content of the fatty acid soap (A) ranges from 30 to 50 wt. %.

8. The framed soap composition according to claim 1, wherein the content of the sodium chloride (B) ranges from 1 to 4 wt. %.

9. The framed soap composition according to claim 1, wherein the content of the sodium sulfate (C) ranges from 0.5 to 4 wt. %.

10. The framed soap composition according to claim 1, wherein the total content of ingredients (B) and (C) ranges from 1.5 to 8 wt. %.

11. The framed soap composition according to claim 1, wherein the total content of ingredients (B) and (C) ranges from 2 to 7 wt. %.

12. The framed soap composition according to claim 1, wherein the total content of ingredients (B) and (C) ranges from 2.5 to 6 wt. %.

13. The framed soap composition according to claim 1, wherein the gas bubbles range in size from 10 μm to 80 μm.

* * * * *